United States Patent [19]

Reichert, Jr.

[11] Patent Number: 4,568,347
[45] Date of Patent: Feb. 4, 1986

[54] INTRAOCULAR LENS

[76] Inventor: Henry L. Reichert, Jr., c/o The Eye Clinic of North Dakota, 620 N. 9th St., Bismarck, N. Dak. 58501

[21] Appl. No.: 569,041

[22] Filed: Jan. 9, 1984

[51] Int. Cl.$^4$ .............................................. A61F 2/16
[52] U.S. Cl. ...................................................... 623/6
[58] Field of Search ................................................ 3/13

[56] References Cited

U.S. PATENT DOCUMENTS

| 4,174,543 | 11/1979 | Kelman | 3/13 |
| 4,377,873 | 3/1983 | Reichert, Jr. | 3/13 |
| 4,418,431 | 12/1983 | Feaster | 3/13 |

OTHER PUBLICATIONS

Lens Styles from Cilco (advertisement brochure), Cilco, Inc., 1616 13th Ave., Box 1680, Huntington, W. Va. 25717, Oct. 1982, pp. 1, 2 & 6, Symmetrical Multiflex Anterior Chamber Lens (styles MT-3-MT-7).

Primary Examiner—Ronald L. Frinks
Attorney, Agent, or Firm—Burd, Bartz & Gutenkauf

[57] ABSTRACT

An implantable artificial intraocular bipod lens comprising a medial light-focusing lens body having fixation elements connected thereto. The fixation elements comprise a pair of elongated relatively thin and narrow legs extending in opposite directions from opposite sides of the lens body. The legs each include three interconnected segments, the corresponding segments of each leg lying in spaced apart parallel relation to one another. The first leg segments are relatively short and extend along substantially tangential lines from opposite sides of the lens body. The second leg segments are relatively longer and extend outwardly away from the lens body and inwardly toward a median line through the lens body. The third leg segments function as foot segments and are relatively short. They are arcuately connected to the outer ends of the second segments and extend outwardly away from the median line in a direction opposite from that of the second segment. A flat circular pad having a manipulation/suture hole is provided at the end of each foot segment.

15 Claims, 5 Drawing Figures

U.S. Patent          Feb. 4, 1986          4,568,347
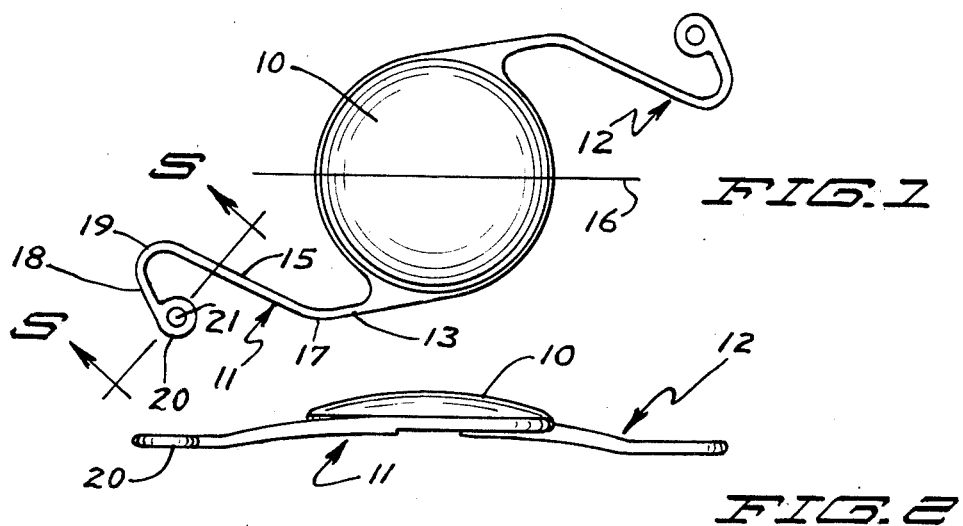
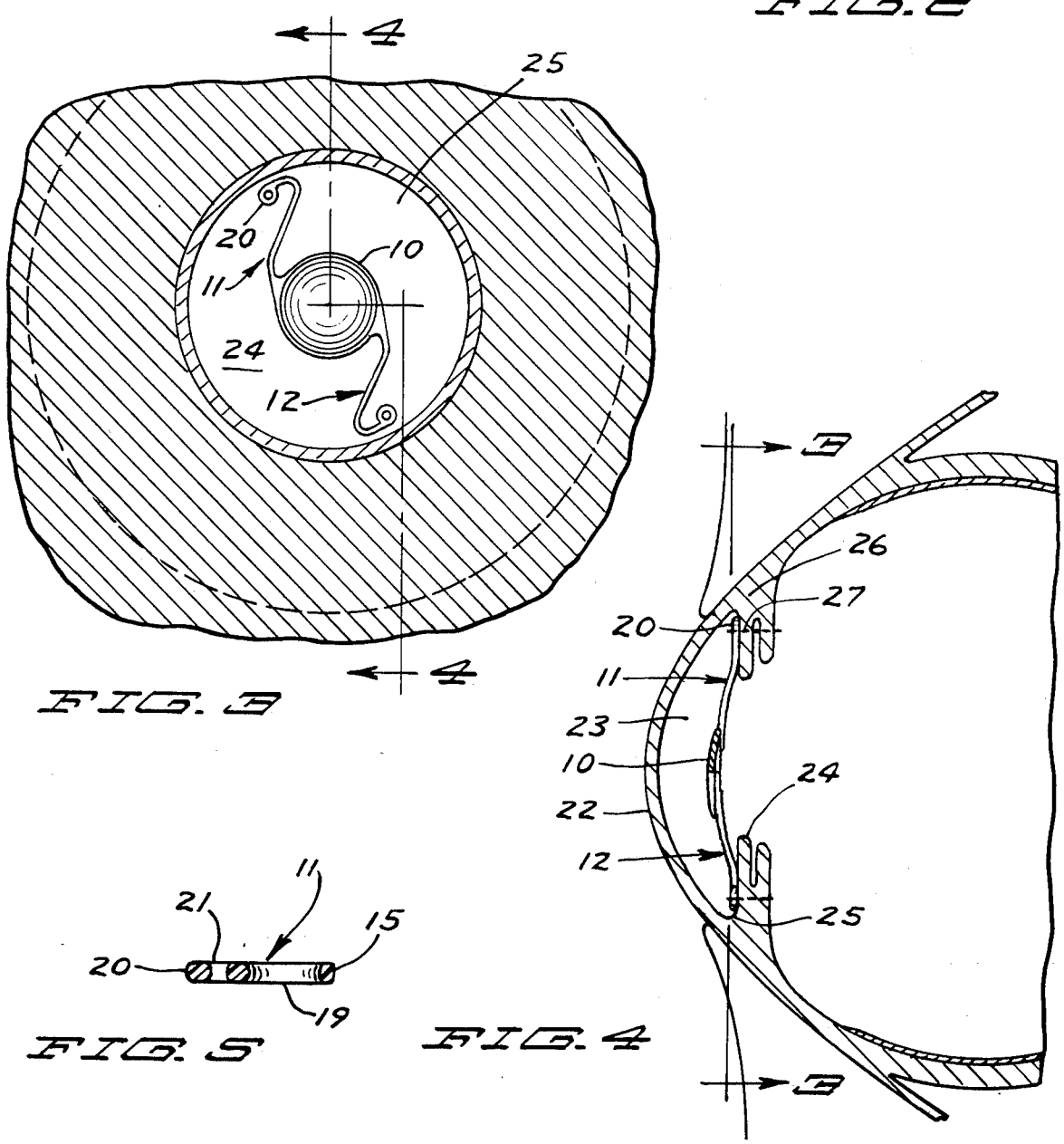

INTRAOCULAR LENS

BACKGROUND OF THE INVENTION

1. Field of the Invention

This invention is directed to an intraocular lens for implantation in the anterior chamber of the eye following intracapsular lens extraction, extracapsular lens extraction or as a secondary implantation.

2. The Prior Art

The intraocular lens of this application represents an improvement over the intraocular bipod lens of applicant's U.S. Pat. No. 4,377,873, issued Mar. 29, 1983. The lens of that patent is characterized by fixation elements in the form of a pair of straight elongated relatively thin and narrow legs extending tangentially in opposite directions from opposite sides of a medial light-focusing lens body and lying along generally parallel lines. A relatively thin and narrow arcuate foot is located at the end of each of the legs. These feet extend obliquely in opposite directions. A suture/manipulation hole is provided in at least one of the legs.

SUMMARY OF THE INVENTION

The intraocular lens of the present invention is based on the same principle of bipod lens support. The design of the legs has been changed to provide greater flexibility. The manipulation hole has been relocated to the tip of the feet.

Broadly stated, the implantable artificial intraocular bipod lens of the present invention comprises a medial generally circular light-focusing plano-convex lens body having a planar base and convex vault, and bipod position fixation elements connected to and integral with the lens body. The fixation elements include a pair of elongated relatively thin and narrow legs. Each leg is composed of three segments. The first leg segments are relatively short and extend along substantially tangential lines in opposite directions from diametrically opposite areas of the lens body, in spaced parallel relation.

The second leg segments are relatively longer and are arcuately connected to and integral with the first segments and then extend outwardly away from the lens body and inwardly toward a median line through the lens body, in spaced parallel relation. The third leg segments are relatively short foot segments arcuately connected to and integral with the second leg segments and extend outwardly away from the median line in a direction opposite from the second segment and in spaced parallel relation.

A flat circular pad is located at the end of each foot segment. The foot segments are tangential to the pad on the outside edge of the pad. A manipulation hole is provided in the center of each pad. A generally triangular gusset connects the first leg segment and the lens body.

BRIEF DESCRIPTION OF THE DRAWINGS

The invention is illustrated by the accompanying drawings in which corresponding parts are identified by the same numerals and in which:

FIG. 1 is a top plan view of the intraocular lens according to the present invention;

FIG. 2 is an elevation thereof;

FIG. 3 is a front elevation, partly in section, on the line 3—3 of FIG. 4 and in the direction of the arrows and showing the lens implanted in an eye;

FIG. 4 is a section on the line 4—4 of FIG. 3 and in the direction of the arrows; and FIG. 5 is a section on the line 5—5 of FIG. 1 and in the direction of the arrows.

DETAILED DESCRIPTION OF THE PREFERRED EMBODIMENT

Referring now to the drawings, the intraocular bipod lens comprises generally a circular plano-convex medial-light focusing lens body 10 and a pair of similar position fixation elements in the form of legs, indicated generally at 11 and 12, and extending outwardly from the lens body in opposite directions from opposite sides of the lens body. The legs 11 and 12 are of identical structure described in detail with reference to leg 11.

Each leg is composed generally of three integral segments. The first leg segments 13 are relatively short and extend along substantially tangential lines in opposite directions from diametrically opposite sides of the lens body in spaced parallel relation to one another. For stability, each leg segment 13 is connected to the lens body by means of a generally triangular gusset 14.

The second leg segments 15 are relatively longer than the first segments and extend in a direction outwardly away from the lens body 10 and inwardly toward a median line 16 through the lens body. The second leg segments 15 are in spaced parallel relation and are joined to the first segment in an integral arcuate connection 17. Typically arcuate connection 17 may have a radius of about 2.3 mm. The first leg segments 13 extend at an angle of about 7° to 13°, preferably about 10°, from median line 16. The second leg segments extend at an angle of about 22° to 28°, preferably about 25°, from median line 16.

The third leg segments 18 are relatively short and function as foot segments. Segments 18 are joined to leg segments 15 by an integral arcuate connection 19 so as to extend outwardly away from the median line 16 in a direction opposite from that of the second segment 15. Typically arcuate connection 19 may have a radius of about 0.60 mm and at its nearest point is spaced from median line 16 by about 1.5 mm. The foot segments 18 are in spaced parallel relation and extend at an angle of about 62° to 68°, preferably about 65°, from median line 16. A flat circular foot pad 20 is located at the end of each leg segment 18 which is tangential to the circular pad on the outside edge thereof. A manipulation/suture hold 21 is provided in the center of pad 20.

For maximum flexibility in the plane of the legs, the leg segments are preferably oval in cross section with the larger dimension in the direction perpendicular to that plane, as best seen in FIG. 5. Thus, the leg segments in cross section may be between about 0.9 to 0.15 mm, preferably about 0.12 mm, in the smaller dimension by about 0.22 to 0.28 mm, preferably about 0.25 mm, in the larger dimension. Each foot pad is typically about 0.75 mm in diameter and about 0.22 to 0.28 mm, preferably about 0.25 mm, in thickness. The manipulation hole/suture hole is typically about 0.30 to 0.35 mm in diameter.

The lens body 10 has a diameter of about 4.5 to 6.5 mm, preferably about 5.5 mm, with a vault measured at the center of about 0.45 to 0.55 mm, preferably about 0.5 mm. The lens has an optical power sufficient to rectify the optical defects of the eye, i.e., between about 12 and 22 diopters of power. The overall diameter of the lens, measured between the outer edges of foot segments 18, may range from about 11.0 to 14.5 mm.

As best seen in FIG. 2, the outer ends of legs 11 and 12 are displaced below the planar base surface of the lens body 10. Preferably this displacement is between about 0.17 to 0.23 mm, preferably about 0.20 mm. Most of the displacement is in leg segments 13 and that half of leg segment 15 closest to the lens body. Typically these portions are very slightly arcuate with a spherical radius between about 14 to 26.5 mm.

The implantable lens may be formed by molding or casting and/or machining or grinding, integrally in one piece, from any of a number of transparent physiologically inert non-toxic biocompatible materials. Exemplary materials include methylmethacrylate resins available under the tradenames Lucite and Plexiglas. A preferred material is the polymethylmethacrylate resin available under the tradename Perspex C. Q. Although made of a generally rigid material, the legs are semi-rigid since the thinness of the legs imparts flexibility aiding greatly in fitting the lens into the eye.

The increased flexibility of the legs of the lens of the present invention, as compared to that of applicant's prior patent, increases the compressibility of the lens with minimal force. This increased flexibility provides greater adaptability of fit in the eye making sizing of the lens a less important factor. Lens measurement prior to insertion is less critical. Fewer stock sizes, one or two instead of three to four, need be kept on hand, simplifying inventory control. The increased flexibility also means that the lens gives or yields somewhat within the eye causing less tendency for the eye to be tender to the touch in the post-operative state.

Referring now to FIGS. 3 and 4, there is shown the manner in which the implantable lens is fitted into the eye. The lens is inserted through an incision in the cornea 22 into the anterior chamber 23 between the cornea and the iris 24. The lens is positioned by use of the manipulation hole 21 with the feet segments 18 placed in such a manner as to achieve fixation in an oblique meridian about 20° to 30°, preferably about 25°, from the vertical, which is the most stable considering both vertical and horizontal line movements.

The foot segments 18 are wedged into the scleral spur 25, the angle at the general meeting place of the cornea 22, iris 24 and sclera 26. The generally flat outer edges of feet segments 18 engage the inner curve of the scleral spur 25 to achieve a slightly greater tension on the edges of the foot segments to minimize rotation. Besides aiding in manipulation of the lens for proper placement, holes 21 may be used in conjunction with sutures 27 to fix the lens to the iris.

The oblique placement of the foot pads facilitates fixation as it is more easily observed during the time of fixation. The suggested placement is from the superior nasal quadrant, the upper quarter nearest the nose, to the inferior temporal quadrant, the lower quadrant away from the nose. This placement utilizes the natural protection afforded by the bony orbit of the eye socket.

As in the case of its predecessor described in U.S. Pat. No. 4,377,873, the bipod lens of this invention offers ease in manufacturing, increased ease in insertion and placement of the lens, minimizing the risk of iris tuck. The simple, sophisticated design also renders insertion through a small incision easier and makes the entire lens system more lightweight. Although shown in one specific configuration, the lens may be made in the mirror image thereof.

It is apparent that many modifications and variations of this invention as hereinbefore set forth may be made without departing from the spirit and scope thereof. The specific embodiments described are given by way of example only and the invention is limited only by the terms of the appended claims.

The embodiments of the invention in which an exclusive property or privilege is claimed are defined as follows:

1. An implantable artificial intraocular bipod two-point contact lens comprising:
   (A) a medial generally circular light-focusing plano-convex lens body having a planar base and convex vault, and
   (B) position fixation elements connected to and integral with said body, said fixation elements including:
      (1) a pair of elongated relatively thin and narrow legs, said legs each including
         (a) a relatively short first segment extending along substantially tangential lines in opposite directions from diametrically opposite areas of the lens body, in spaced parallel relation, at an angle of about 7° to 13° from a median line through the lens body,
         (b) a relatively longer second segment arcuately connected to and integral with the first segment and then extending outwardly away from the lens body and inwardly toward said median line through the lens body, without crossing said median line, said second leg segments being in spaced parallel relation, and
         (c) a relatively short third one-point contact foot segment arcuately connected to and integral with the second segment and extending outwardly away from said median line in a direction opposite from said second segment, in spaced parallel relation, and
      (2) a flat circular pad at the end of said foot segment,
         (a) said foot segment being tangential to said pad on the outside edge thereof,
         (b) a manipulation hole in the center of said pad, and
      (3) a generally triangular gusset connecting said first leg segment and lens body.

2. An implantable artificial intraocular bipod lens according to claim 1 wherein:
   (A) said second leg segment extends at an angle of about 22° to 28° from said median line, and
   (B) said third segment extends at an angle of about 62° to 68° from said median line.

3. An implantable artificial intraocular bipod lens according to claim 2 wherein:
   (A) said first leg segment extends at an angle of about 10° from said median line,
   (B) said second leg segment extends at an angle of about 25° from said median line, and
   (C) said third leg segment extends at an angle of about 65° from said median line.

4. An implantable artificial intraocular bipod lens according to claim 1 wherein the ends of the fixation elements are displaced below the planar base surface of the lens body.

5. An implantable artificial intraocular bipod lens according to claim 4 wherein the fixation elements are displaced below the planar base surface of the lens body by about 0.17 to 0.23 mm.

6. An implantable artificial intraocular bipod lens according to claim 1 wherein said leg segments are generally oval in cross section and about 0.09 to 0.15 mm in one direction and about 0.22 to 0.28 mm in the other.

7. An implantable artificial intraocular bipod lens according to claim 1 wherein said foot pad is about 0.75 mm in diameter, about 0.22 to 0.28 mm thick, and said manipulation hole is about 0.30 to 0.35 mm in diameter.

8. An implantable artificial intraocular bipod lens according to claim 1 wherein:
   (A) said lens body has a diameter of about 4.5 to 6.5 mm with a center vault of about 0.45 to 0.55 mm, and
   (B) the overall diameter of the lens between the outer edges of the feet segments is from about 11.0 to 14.5 mm.

9. An implantable artificial intraocular bipod lens according to claim 1 wherein said lens is formed from a physiologically inert, non-toxic, biocompatible synthetic resinous material.

10. An implantable artificial intraocular bipod lens according to claim 9 wherein said lens is formed from polymethylmethacrylate.

11. An implantable artificial intraocular bipod two-point contact lens comprising:
   (A) a medial generally circular light-focusing plano-convex lens body having a planar base and convex vault, said lens body having a diameter of about 4.5 to 6.5 mm with a center vault of about 0.45 to 0.55 mm, and
   (B) position fixation elements connected to and integral with said lens body, said fixation elements being displaced below the planar base surface of the lens body by about 0.17 to 0.23 mm, and including:
      (1) a pair of elongated relatively thin and narrow legs, said legs each including
         (a) a relatively short first segment extending along substantially tangential lines in opposite directions from diametrically opposite areas of the lens body, in spaced parallel relation at an angle between about 7° to 13° from a median line through the lens body,
         (b) a relatively longer second segment arcuately connected to and integral with the first segment and then extending outwardly away from the lens body and inwardly toward said median line in spaced parallel relation at an angle of about 22° to 28° from said median line, and
         (c) a relatively short third foot segment arcuately connected to and integral with the second segment and extendng outwardly from said median line in a direction opposite from said second segment in spaced parallel relation at an angle of about 62° to 68° from said median line,
      (2) a flat circular pad about 0.75 mm in diameter and about 0.22 to 0.28 mm thick at the end of said foot segment,
         (a) said foot segment being tangential to said pad on the outside edge thereof,
         (b) a manipulation hole about 0.30 to 0.35 mm in diameter in the center of said pad, and
      (3) a generally triangular gusset connecting said first leg segment and lens body.

12. An implantable artificial intraocular bipod lens according to claim 11 wherein said leg segments are generally oval in cross section and about 0.09 to 0.15 mm in one direction and about 0.22 to 0.28 mm in the other.

13. An implantable artificial intraocular bipod lens according to claim 11 wherein:
   (A) said lens body has a diameter of about 5.5 mm with a center vault of about 0.5 mm,
   (B) the fixation elements are displaced below the planar base surface of the lens body by about 0.20 mm,
   (C) said leg segments are generally oval in cross section and about 0.12 mm in one direction and about 0.25 mm in the other,
   (D) said first leg segment extends at an angle of about 10° from said median line,
   (E) said second leg segment extends at an angle of about 25° from said median line,
   (F) said third leg segment extends at an angle of about 65° from said median line, and
   (G) the overall diameter of the lens between the outer edges of the feet segments is from about 11.0 to 14.5 mm.

14. An implantable artificial intraocular bipod lens according to claim 11 wherein the lens is formed from a physiologically inert, non-toxic, biocompatible synthetic resinous material.

15. An implantable artificial intraocular bipod lens according to claim 14 wherein said lens is formed from polymethylmethacrylate.

* * * * *

UNITED STATES PATENT AND TRADEMARK OFFICE
CERTIFICATE OF CORRECTION

PATENT NO. : 4,568,347

DATED : February 4, 1986

INVENTOR(S) : Henry L. Reichert, Jr.

It is certified that error appears in the above-identified patent and that said Letters Patent is hereby corrected as shown below:

Column 3, line 27, "to" should be --or--.

Column 3, line 41, after "movements.", insert --As seen, the lens makes two-point contact with one point of contact on each side, or bipod type contact.--

Column 6, line 5, "extendng" should be --extending--.

Signed and Sealed this

Twenty-ninth Day of July 1986

[SEAL]

Attest:

Attesting Officer

DONALD J. QUIGG

Commissioner of Patents and Trademarks